(12) United States Patent
Inghardt et al.

(10) Patent No.: US 6,433,186 B1
(45) Date of Patent: Aug. 13, 2002

(54) AMIDINO DERIVATIVES AND THEIR USE AS THORMBIN INHIBITORS

(75) Inventors: Tord Inghardt, Frillesås; Arne N. Svensson, Mölndal, both of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/900,903

(22) Filed: Jul. 10, 2001

(30) Foreign Application Priority Data

Aug. 16, 2000 (SE) ................................ 0002921
Aug. 16, 2000 (SE) ................................ 0002922

(51) Int. Cl.$^7$ ........................ C07D 207/04; A61K 31/40
(52) U.S. Cl. ........................ 548/566; 548/571; 548/950; 514/428
(58) Field of Search ................ 548/566, 571, 548/950

(56) References Cited

U.S. PATENT DOCUMENTS

| | | | |
|---|---|---|---|
| 4,346,078 A | | 8/1982 | Bajusz et al. ............... 424/177 |
| 5,710,130 A | * | 1/1998 | Schacht et al. ............... 514/19 |
| 5,925,667 A | * | 7/1999 | Nishino et al. ............. 514/428 |

FOREIGN PATENT DOCUMENTS

| | | |
|---|---|---|
| EP | 0 185 390 | 6/1986 |
| EP | 0 195 212 | 9/1986 |
| EP | 0 293 881 | 12/1988 |
| EP | 0 362 002 | 4/1990 |
| EP | 0 364 344 | 4/1990 |
| EP | 0 468 231 | 1/1992 |
| EP | 0 526 877 | 2/1993 |
| EP | 0 530 167 | 3/1993 |
| EP | 0 542 525 | 5/1993 |
| EP | 0 559 046 | 9/1993 |
| EP | 0 641 779 | 3/1995 |
| EP | 0 648 780 | 4/1995 |
| EP | 0 669 317 | 8/1995 |
| WO | 97/46577 | 12/1977 |
| WO | 93/11152 | 6/1993 |
| WO | 93/18060 | 9/1993 |
| WO | 94/29336 | 12/1994 |
| WO | 98/23609 | 9/1995 |
| WO | 95/35309 | 12/1995 |
| WO | 96/03374 | 2/1996 |
| WO | 96/25426 | 8/1996 |
| WO | 96/31504 | 10/1996 |
| WO | 96/32110 | 10/1996 |
| WO | 97/02284 | 1/1997 |
| WO | 97/23499 | 7/1997 |
| WO | 97/33576 | 9/1997 |
| WO | 97/49404 | 12/1997 |
| WO | 98/06740 | 2/1998 |
| WO | 98/57932 | 12/1998 |
| WO | 99/29664 | 6/1999 |
| WO | 00/35869 | 6/2000 |
| WO | 00/42059 | 7/2000 |

OTHER PUBLICATIONS

Claesson, "Synthetic peptides and peptidomimetics . . . ," Blood Coagul. Fibrinol., vol. 5, p. 411 (1994).
Blomback et al, "Synthetic Peptides with . . . ," J. Clin. Lab. Invest., vol. 24, suppl. 107, p. 59 (1969).

* cited by examiner

Primary Examiner—Taofiq Solola
Assistant Examiner—Golam M. M. Shameem
(74) Attorney, Agent, or Firm—Nixon & Vanderhye

(57) ABSTRACT

There is provided compounds of formula I,

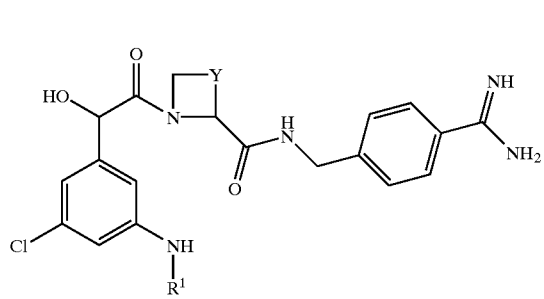

wherein Y and $R^1$ have meanings given in the description, and pharmaceutically acceptable derivatives (including prodrugs) thereof, which compounds and derivatives are useful as, or are useful as prodrugs of, competitive inhibitors of trypsin-like proteases, such as thrombin, and thus, in particular, in the treatment of conditions where inhibition of thrombin is required (e.g. thrombosis) or as anticoagulants.

28 Claims, No Drawings

AMIDINO DERIVATIVES AND THEIR USE AS THORMBIN INHIBITORS

FIELD OF THE INVENTION

This invention relates to novel pharmaceutically useful compounds, in particular compounds that are, and/or compounds that are metabolised to compounds which are, competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would be expected to exhibit antithrombotic activity. In addition, antithrombotic activity would be expected to be enhanced by effective inhibition of the positive feedback mechanism.

PRIOR ART

The early development of low molecular weight inhibitors of thrombin has been described by Claesson in Blood Coagul. Fibrinol. (1994) 5, 411.

Blombäck et al (in J. Clin. Lab. Invest. 24, suppl. 107, 59, (1969)) reported thrombin inhibitors based on the amino acid sequence situated around the cleavage site for the fibrinogen Aα chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based on dipeptidyl derivatives with an α,ω-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position (International Patent Application WO 97/23499 discloses prodrugs of certain of these compounds); European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidino-piperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters and amides, European Patent Application 0 362 002 fluoroalkylamide ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl derivatives have been disclosed in European Patent Application 0 669 317 and International Patent Applications WO 95/35309, WO 95/23609, WO 96/25426, WO 97/02284, WO 97/46577, WO 96/32110, WO 96/31504, WO 96/03374, WO 98/06740, WO 97/49404, WO 98/57932, WO 99/29664 and WO 00/35869. In particular WO 97/02284 and WO 00/42059 disclose thrombin inhibitors with substituted mandelic acids in the P3 position.

However, there remains a need for effective inhibitors of trypsin-like serine proteases, such as thrombin. There is also a need for compounds which have a favourable pharmacokinetic profile (e.g. low clearance) and are selective in inhibiting thrombin over other serine proteases, in particular those involved in haemostatis. Compounds which exhibit competitive inhibitory activity towards thrombin would be expected to be especially useful as anticoagulants and therefore in the therapeutic treatment of thrombosis and related disorders.

DISCLOSURE OF THE INVENTION

According to the invention there is provided compounds of formula I,

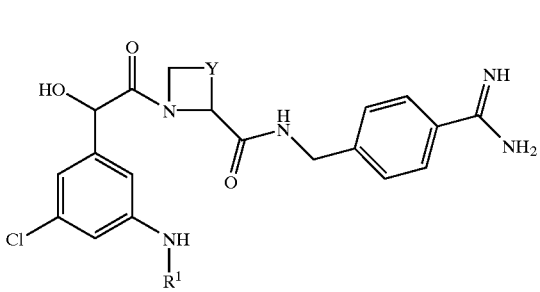

wherein
$R^1$ represents $C(O)CH_3$ or $C_{1-3}$ alkyl; and
Y represents —$CH_2$— or —$(CH_2)_2$—,
and pharmaceutically-acceptable derivatives thereof.
The term "pharmaceutically-acceptable derivatives" includes inter alia pharmaceutically-acceptable salts (e.g. acid addition salts).

Preferred compounds of formula I include those in which:
R¹ represents C(O)CH₃, methyl or ethyl;
Y represents —CH₂—.
Particularly preferred compounds of formula I include
Ph(3-Cl)(5-NHMe)—CH(OH)C(O)-Aze-Pab;
Ph(3-Cl)(5-NHAc)—CH(OH)C(O)-Aze-Pab.
Abbreviations are listed at the end of this specification.

Compounds of formula I may be made in accordance with techniques well known to those skilled in the art, for example as described hereinafter.

According to a further aspect of the invention there is provided a process for the preparation of a compound of formula I, which comprises:

(i) the coupling of a compound of formula II wherein R¹ is as hereinbefore defined, with a compound of formula III, wherein Y is as hereinbefore defined, for example in the presence of a coupling agent (e.g. oxalyl chloride in DMF, EDC, DCC, HBTU, HATU, PyBOP or TBTU), an appropriate base (e.g. pyridine, DMAP, TEA, 2,4,6-collidine or DIPEA) and a suitable organic solvent (e.g. dichloromethane, acetonitrile, EtOAc or DMF);

(ii) the coupling of a compound of formula IV, wherein R¹ and Y are as hereinbefore defined, with para-amidinobenzylamine, for example under conditions as described in step (i) above; or (iii) deprotection of a protected derivative of a compound of formula I under standard conditions.

Compounds of formula I may be prepared by way of deprotection of a corresponding compound of formula XV, as defined hereinafter, which deprotection comprises removal of the group C(O)OR$^x$, in which R$^x$ is as defined hereinafter, from the compound of formula XV, for example under conditions known to those skilled in the art (e.g. by reacting with QF or TFA (e.g. as described hereinafter)).

Further, compounds of formula I may be prepared by way of deprotection of a corresponding compound of formula Ia, as defined hereinafter, in which R² represents OR³, wherein R² and R³ are as defined hereinafter, for example by hydrogenation in the presence of a suitable catalyst (e.g. a supported metal catalyst such as Pd/C (e.g. 10% (w/w) Pd/C)) and an appropriate solvent (e.g. a lower (e.g. C$_{1-6}$) alkyl alcohol such as ethanol), and optionally in the presence of a suitable acid (e.g. acetic acid).

Compounds of formula II are available using known and/or standard techniques.

For example, compounds of formula II may be prepared by reaction of an aldehyde of formula V, wherein R¹ is as hereinbefore defined with:

(a) a compound of formula VI, $$R''CN \qquad\qquad VI$$

wherein R" represents H or (CH₃)₃Si, for example at room, or elevated, temperature (e.g. below 100° C.) in the presence of a suitable organic solvent (e.g. chloroform or methylene chloride) and, if necessary, in the presence of a suitable base (e.g. TEA) and/or a suitable catalyst system (e.g. benzylammonium chloride or zinc iodide), followed by hydrolysis under conditions that are well known to those skilled in the art (e.g. as described hereinafter);

(b) NaCN or KCN, for example in the presence of NaHSO₃ and water, followed by hydrolysis;

(c) chloroform, for example at elevated temperature (e.g. above room temperature but below 100° C.) in the presence of a suitable organic solvent (e.g. chloroform) and, if necessary, in the presence of a suitable catalyst system (e.g. benzylammonium chloride), followed by hydrolysis;

(d) a compound of formula VII, wherein M represents Mg or Li, followed by oxidative cleavage (e.g. ozonolysis or osmium or ruthenium catalysed) under conditions which are well known to those skilled in the art; or (e) tris(methylthio)methane under conditions which are well known to those skilled in the art, followed by hydrolysis in the presence of e.g. HgO and HBF₄.

Compounds of formula II may alternatively be prepared from Ph(3-Cl)(5-NH₂)—CH(OH)C(O)OH, for example as described hereinafter for compounds of formula II in which R¹ represents C(O)CH₃ or methyl.

The enantiomeric forms of the compound of formula II (i.e. those compounds having different configurations of substituents about the C-atom α- to the CO₂H group) may be separated by an enantiospecific derivatisation step. This may be achieved, for example by an enzymatic process. Such enzymatic processes include, for example, transesterification of the α-OH group at between room and reflux temperature (e.g. at between 45 and 65° C.) in the presence of a suitable enzyme (e.g. Lipase PS Amano), an appropriate ester (e.g. vinyl acetate) and a suitable solvent (e.g. methyl tert-butyl ether). The derivatised isomer may then be separated from the unreacted isomer by conventional separation techniques (e.g. chromatography).

Groups added to compounds of formula II in such a derivatisation step may be removed either before any further reactions or at any later stage in the synthesis of compounds of formula I. The additional groups may be removed using conventional techniques (e.g. for esters of the α-OH group, hydrolysis under conditions known to those skilled in the art (e.g. at between room and reflux temperature in the presence of a suitable base (e.g. NaOH) and an appropriate solvent (e.g. MeOH, water or mixtures thereof))).

Compounds of formula IV may be prepared by coupling a compound of formula II as hereinbefore defined to a compound of formula VIII,

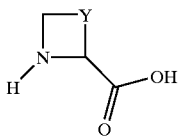

VIII wherein Y is as hereinbefore defined, for example under similar conditions to those described herein for preparation of compounds of formula I.

Compounds of formula V are available using known and/or standard techniques. For example, they may be prepared by:
(i) reduction of a compound of formula X,

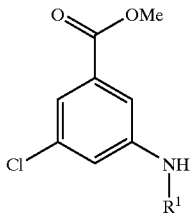

X wherein $R^1$ is as hereinbefore defined, or a protected derivative thereof, in the presence of a suitable reducing agent (e.g. DIBAL-H); or
(ii) oxidation of a compound of formula XI,

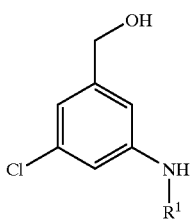

XI wherein $R^1$ is as hereinbefore defined, or a protected derivative thereof, in the presence of a suitable oxidising agent (e.g. $MnO_2$, pyridinium chlorochromate or a combination of DMSO and oxalyl chloride).

Compounds of formulae III, VI, VII, VIII, X and XI are either commercially available, are known in the literature, or may be obtained either by analogy with the processes described herein, or by conventional synthetic procedures, in accordance with standard techniques, from readily available starting materials using appropriate reagents and reaction conditions (e.g. as described hereinafter).

Compounds of formula I may be isolated from their reaction mixtures using conventional techniques.

In accordance with the present invention, pharmaceutically acceptable derivatives of compounds of formula I also include "protected" derivatives, and/or compounds that act as prodrugs, of compounds of formula I.

Compounds that may act as prodrugs of compounds of formula I that may be mentioned include compounds of formula Ia,

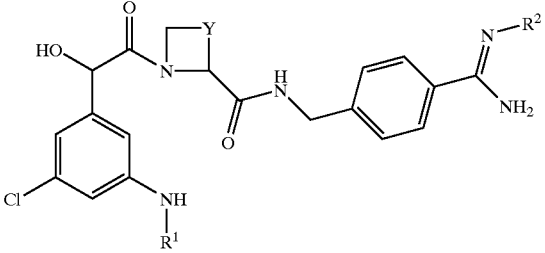

Ia wherein $R^2$ represents $OR^3$ or $C(O)OR^4$;
$R^3$ represents H, $C_{1-10}$ alkyl, $C_{1-3}$ alkylaryl or $C_{1-3}$ alkyloxyaryl (the alkyl parts of which latter two groups are optionally interrupted by one or more oxygen atoms, and the aryl parts of which latter two groups are optionally substituted by one or more substituents selected from halo, phenyl, methyl or methoxy, which latter three groups are also optionally substituted by one or more halo substituents);
$R^4$ represents $C_{1-10}$ alkyl (which latter group is optionally interrupted by one or more oxygen atoms), or $C_{1-3}$ alkylaryl or $C_{1-3}$ alkyloxyaryl (the alkyl parts of which latter two groups are optionally interrupted by one or more oxygen atoms, and the aryl parts of which latter two groups are optionally substituted by one or more substituents selected from halo, phenyl, methyl or methoxy, which latter three groups are also optionally substituted by one or more halo substituents); and
$R^1$ and Y are as hereinbefore defined,
and pharmaceutically-acceptable derivatives thereof.

The term "pharmaceutically-acceptable derivatives" of compounds of formula Ia includes pharmaceutically-acceptable salts (e.g. acid addition salts).

Alkyloxyaryl groups that $R^3$ and $R^4$ may represent comprise an alkyl and an aryl group linked by way of an oxygen atom. Alkylaryl and alkyloxyaryl groups are linked to the rest of the molecule via the alkyl part of those groups, which alkyl parts may (if there is a sufficient number (i.e. three) of carbon atoms) be branched-chain. The aryl parts of alkylaryl and alkyloxyaryl groups which $R^3$ and $R^4$ may represent include carbocyclic and heterocyclic aromatic (heteroaryl) groups, such as phenyl, naphthyl, pyridinyl, oxazolyl, isoxazolyl, thiadiazolyl (e.g. 1,2,3-thiadiazolyl), indolyl and benzofuranyl and the like.

Alkyl groups which $R^3$ and $R^4$ may represent may be straight-chain or, when there is a sufficient number (i.e. a minimum of three) of carbon atoms, be branched-chain and/or cyclic. Further, when there is a sufficient number (i.e. a minimum of four) of carbon atoms, such alkyl groups may also be part cyclic/acyclic. Such alkyl groups may also be saturated or, when there is a sufficient number (i.e. a minimum of two) of carbon atoms, be unsaturated.

Halo groups with which $R^3$ and $R^4$ may be substituted include fluoro, chloro, bromo and iodo.

When R² represents C(O)OR⁴, preferred R⁴ groups include:

(a) linear, branched or cyclic C₃₋₆ alkyl, for example C₄₋₆ cycloalkyl;
(b) C₁₋₂ alkylaryl groups, such as benzyl, optionally substituted as indicated hereinbefore.

Preferred compounds of formula Ia include those in which R² represents OR³.

When R² represents OR³, preferred R³ groups include:
(a) H;
(b) unsubstituted, linear, branched or cyclic C₁₋₈ (e.g. C₁₋₆) alkyl, such as linear C₁₋₃ alkyl (e.g. methyl, ethyl or i-propyl), branched C₃₋₈ alkyl (e.g. i-butyl) or cyclic C₄₋₇ alkyl (e.g. cyclobutyl or cyclohexyl);
(c) C₁₋₃ alkyloxyphenyl (e.g. C₂ alkyloxyphenyl), the phenyl group of which is optionally substituted by one or more substituents as indicated hereinbefore (e.g. trifluoromethyl);
(d) C₁₋₂ alkylaryl (e.g. methylaryl), wherein the aryl group is phenyl, pyridinyl, isoxazolyl or thiadiazolyl, which latter four groups are optionally substituted by one or more substituents as indicated hereinbefore (e.g. methoxy, methyl, bromo and/or chloro).

Preferred compounds of formula Ia include those in which R² represents OR³ and R³ represents:
(i) linear or cyclic (as appropriate), C₁₋₆ (e.g. C₁₋₄) alkyl, such as methyl, ethyl, i-propyl or cyclohexyl; or
(ii) methylaryl, wherein the aryl group is phenyl or isoxazolyl, which latter two groups are optionally substituted in the aryl part by one substituent selected from methoxy, methyl and bromo (e.g. 4-methylbenzyl, 3-methoxybenzyl, 2-bromobenzyl or 5-methyl-3-isoxazolyl).

Compounds of formula Ia may be prepared by one or more of the following methods:

(a) the coupling of a compound of formula II as hereinbefore defined with a compound of formula XII,

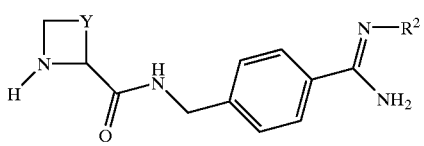

XII wherein Y and R² are as hereinbefore defined, for example under similar conditions to those described hereinbefore for synthesis of compounds of formula I;

(b) the coupling of a compound of formula IV, as hereinbefore defined, with a compound of formula XIII,

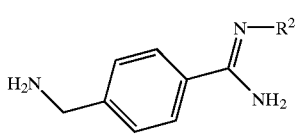

XIII wherein R² is as hereinbefore defined, for example under similar conditions to those described hereinbefore for synthesis compounds of formula I;

(c) for compounds of formula Ia in which R² represents OH, reaction of a corresponding compound of formula XIV,

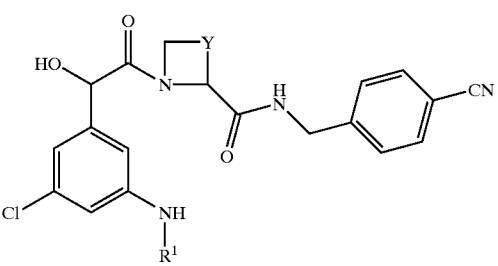

XIV wherein R¹ and Y are as hereinbefore defined, with hydroxylamine, for example under conditions known to those skilled in the art;

(d) for compounds of formula Ia in which R² represents OR³, reaction of a protected derivative of a corresponding compound of formula I which is, for example, a compound of formula XV,

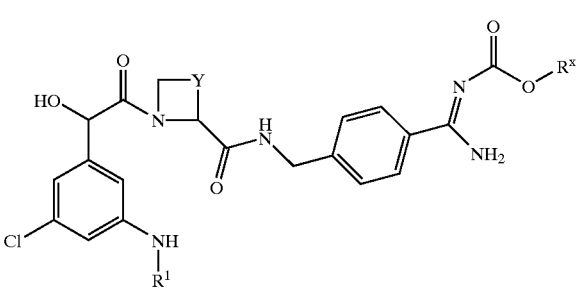

XV wherein R$^x$ represents, for example, —CH₂CH₂—Si(CH₃)₃ or benzyl, and R¹ and Y are as hereinbefore defined, or a tautomer thereof, with a compound of formula XVI,

R³ONH₂    XVI wherein R³ is as hereinbefore defined, or an acid addition salt thereof, for example at between room and reflux temperature in the presence of an appropriate organic solvent (e.g. THF, CH₃CN, DMF or DMSO), followed by removal of the —C(O)OR$^x$ group under conditions known to those skilled in the art (e.g. by reacting with QF or TFA (e.g. as described hereinafter));

(e) for compounds of formula Ia in which R² represents COOR⁴, reaction of a corresponding compound of formula I, as hereinbefore defined, with a compound of formula XVII,

L¹COOR⁴    XVII wherein L¹ represents a suitable leaving group, such as halo, and R⁴ is as hereinbefore defined, for example at or around room temperature in the presence of suitable base (e.g. NaOH, for example in aqueous solution) and an appropriate organic solvent (e.g. methylene chloride); or (f) for compounds of formula Ia in which R² represents OCH₃ or OCH₂CH₃, reaction of a corresponding compound of formula Ia in which R² represents OH with dimethylsulfate or diethylsulfate, respectively, for example in the presence of a suitable base (e.g. an alkali metal hydroxide such as KOH (for example in aqueous solution at e.g. 50 wt. %))

and an appropriate catalyst (e.g. a quaternary ammonium halide such as benzyltrimethylammonium chloride (for example in CH$_2$Cl$_2$ or THF solution at e.g. 10 wt. %)).

Compounds of formula XIV and XV may be prepared by the coupling of a corresponding compound of formula II to, respectively, a compound of formula XVIII,

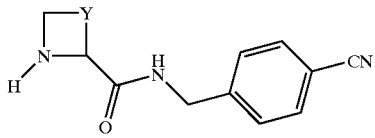

XVIII wherein Y is as hereinbefore defined, or a compound of formula XIX,

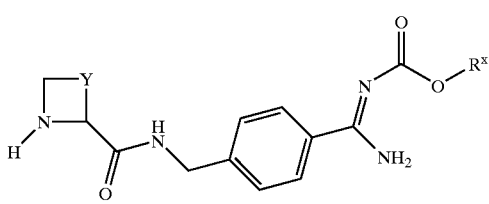

XIX wherein Y and R$^x$ are as hereinbefore defined, for example in each case under similar conditions to those described hereinbefore for synthesis compounds of formula I.

Compounds of formula XIV and XV may alternatively be prepared by coupling of a corresponding compound of formula IV to, respectively, para-cyanobenzylamine, or a compound of formula XX,

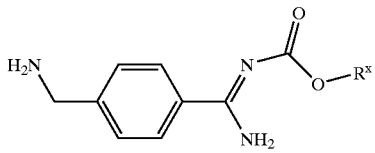

XX wherein R$^x$ is as hereinbefore defined, for example in each case under similar conditions to those described hereinbefore for synthesis compounds of formula I.

Compounds of formula XV may alternatively be prepared by reaction of a corresponding compound of formula XIV with hydroxylamine under conditions known to those skilled in the art, followed by:
  (i) reduction of the resulting hydroxyamidine under conditions known to those skilled in the art (e.g. by catalytic hydrogenation); and then
  (ii) reaction of the resulting compound of formula I with a compound corresponding to a compound of formula XVII in which, in place of R$^4$, the group R$^x$ is present, in which R$^x$ is as hereinbefore defined, for example under conditions described above in respect of the preparation of compounds of formula Ia.

Compounds of formulae XII, XVIII and XIX may be prepared by the coupling of a corresponding compound of formula VIII, as hereinbefore defined, to, respectively, a compound of formula XIII as hereinbefore defined, para-cyanobenzylamine, or a compound of formula XX as hereinbefore defined, for example in each case under similar conditions to those described hereinbefore for synthesis of compounds of formula I.

Compounds of formulae XIII, XVI, XVII and XX are either commercially available, are known in the literature, or may be obtained either by analogy with the processes described herein, or by conventional synthetic procedures, in accordance with standard techniques, from readily available starting materials using appropriate reagents and reaction conditions (e.g. as described hereinafter).

Compounds of formula Ia may be isolated from their reaction mixtures using conventional techniques.

Compounds of formula I and Ia, as defined above, and derivatives of either, are referred to hereinafter as "the compounds of the invention".

The compounds of the invention may exhibit tautomerism. All tautomeric forms and mixtures thereof are included within the scope of the invention. Particular tautomeric forms that may be mentioned include those connected with the position of the double bond in the amidine functionality in a compound of formula Ia, and the position of the substituent R$^2$.

Compounds of the invention also contain two or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Compounds of the invention in which the

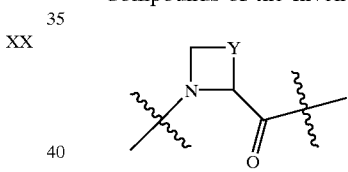

fragment is in the S-configuration are preferred.

Compounds of the invention in which the

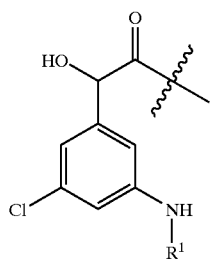

fragment is in the R-configuration are preferred.

The wavy lines on the bonds in the above fragments signify the bond positions of the fragments.

Thus, particularly preferred compounds of the invention include
  Ph(3-Cl)(5-NHMe)-(R)CH(OH)C(O)-(S)Aze-Pab; and
  Ph(3-Cl)(5-NHAc)-(R)CH(OH)C(O)-(S)Aze-Pab.

It will be appreciated by those skilled in the art that in the processes described above and hereinafter the functional groups of intermediate compounds may need to be protected by protecting groups.

Functional groups that it is desirable to protect include hydroxy, amino and carboxylic acid. Suitable protecting groups for hydroxy include trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino and amidino include t-butyloxycarbonyl, benzyloxycarbonyl or 2-trimethylsilylethoxycarbonyl (Teoc). Amidino nitrogens may also be protected by hydroxy or alkoxy groups, and may be either mono- or diprotected.

The protection and deprotection of functional groups may take place before or after coupling, or before or after any other reaction in the abovementioned schemes.

Protecting groups may be removed in accordance with techniques that are well known to those skilled in the art and as described hereinafter.

Persons skilled in the art will appreciate that, in order to obtain compounds of the invention in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", $3^{rd}$ edition, T W Greene & P G M Wutz, Wiley-Interscience (1999).

Protected derivatives of compounds of the invention may be converted chemically to compounds of the invention using standard deprotection techniques (e.g. hydrogenation). The skilled person will also appreciate that certain compounds of formula Ia may also be referred to as being "protected derivatives" of compounds of formula I.

Some of the intermediates referred to hereinbefore are novel.

According to a further aspect of the invention there is thus provided: (a) a compound of formula II as hereinbefore defined or a protected derivative thereof; (b) a compound of formula IV, as hereinbefore defined, or a protected derivative thereof; (c) a compound of formula XIV, as hereinbefore defined, or a protected derivative thereof; and (d) a compound of formula XV, as hereinbefore defined, or a protected derivative thereof.

Preferred compounds of formula II include Ph(3-Cl)(5-NHMe)—CH(OH)C(O)OH and Ph(3-Cl)(5-NHAc)—CH(OH)C(O)OH. Preferred compounds of formula III include Ph(3-Cl)(5-NHMe)—CH(OH)C(O)-Aze-OH and Ph(3-Cl)(5-NHAc)—CH(OH)C(O)-Aze-OH. Preferred compounds of formula XV include Ph(3-Cl)(5-NHMe)—CH(OH)C(O)-Aze-Pab(Teoc) and Ph(3-Cl)(5-NHAc)—CH(OH)C(O)-Aze-Pab(Teoc).

Medical and Pharmaceutical Use

Compounds of the invention may possess pharmacological activity as such. Compounds of the invention that may possess such activity include, but are not limited to, compounds of formula I.

However, other compounds of the invention (including compounds of formula Ia) may not possess such activity, but may be administered parenterally or orally, and may thereafter be metabolised in the body to form compounds that are pharmacologically active (including, but not limited to, corresponding compounds of formula I). Such compounds (which also includes compounds that may possess some pharmacological activity, but that activity is appreciably lower than that of the "active" compounds to which they are metabolised), may therefore be described as "prodrugs" of the active compounds.

Thus, the compounds of the invention are useful because they possess pharmacological activity and/or are metabolised in the body following oral or parenteral administration to form compounds which possess pharmacological activity. The compounds of the invention are therefore indicated as pharmaceuticals.

According to a further aspect of the invention there is thus provided the compounds of the invention for use as pharmaceuticals.

In particular, compounds of the invention are potent inhibitors of thrombin either as such and/or (e.g. in the case of prodrugs), are metabolised following administration to form potent inhibitors of thrombin, for example as may be demonstrated in the tests described below. By "prodrug of a thrombin inhibitor", we include compounds that form (i.e. are metabolised to) a thrombin inhibitor, in an experimentally-detectable amount, and within a predetermined time (e.g. about 1 hour), following oral or parenteral administration (see, for example, Test E below) or, alternatively, following incubation in the presence of liver microsomes (see, for example, Test G below).

The compounds of the invention are thus expected to be useful in those conditions where inhibition of thrombin is required, and/or conditions where anticoagulant therapy is indicated, including the following:

The treatment and/or prophylaxis of thrombosis and hypercoagulability in blood and/or tissues of animals including man. It is known that hypercoagulability may lead to thrombo-embolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis, as well as coagulation syndromes (e.g. disseminated intravascular coagulation (DIC)) and vascular injury in general (e.g. due to surgery).

The treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis (e.g. DVT) and pulmonary embolism, arterial thrombosis (e.g. in myocardial infarction, unstable angina, thrombosis-based stroke and peripheral arterial thrombosis), and systemic embolism usually from the atrium during atrial fibrillation or from the left ventricle after transmural myocardial infarction, or caused by congestive heart failure; prophylaxis of re-occlusion (i.e. thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease and the formation of atherosclerotic plaques, cerebral arterial disease, cerebral infarction, cerebral thrombosis, cerebral embolism, peripheral arterial disease, ischaemia, angina (including unstable angina), reperfusion damage, restenosis after percutaneous trans-luminal angioplasty (PTA) and coronary artery bypass surgery.

Compounds of the invention that inhibit trypsin and/or thrombin may also be useful in the treatment of pancreatitis.

The compounds of the invention are thus indicated both in the therapeutic and/or prophylactic treatment of these conditions.

According to a further aspect of the present invention, there is provided a method of treatment of a condition where inhibition of thrombin is required which method comprises administration of a therapeutically effective amount of a compound of the invention to a person suffering from, or susceptible to, such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising active compound either as a free base, or a pharmaceutically acceptable non-toxic organic or inorganic acid addition salt, or other derivative, in a pharmaceutically acceptable dosage form.

Depending upon the disorder and patient to be treated and the route of administration, the compositions may be administered at varying doses.

The compounds of the invention may also be combined and/or co-administered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists and inhibitors of carboxypeptidase U (CPU).

The compounds of the invention may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is thus provided a pharmaceutical formulation including a compound of the invention, in admixture with a pharmaceutically acceptable adjuvant, diluent or carrier.

Suitable daily doses of the compounds of the invention in therapeutic treatment of humans are about 0.001–100 mg/kg body weight at peroral administration and 0.001–50 mg/kg body weight at parenteral administration.

The compounds of the invention have the advantage that they may be more efficacious, be less toxic, be longer acting, have a broader range of activity, be more potent, produce fewer side effects, be more easily absorbed, and/or have a better pharmacokinetic profile (e.g. lower clearance), than, or have other useful pharmacological, physical, or chemical, properties over, compounds known in the prior art.

Biological Tests

The following test procedures may be employed.

Test A

Determination of Thrombin Clotting Time (TT)

The inhibitor solution (25 μL) is incubated with plasma (25 μL) for three minutes. Human thrombin (T 6769; Sigma Chem. Co or Hematologic Technologies) in buffer solution, pH 7.4 (25 μL, 4.0 NIH units/mL), is then added and the clotting time measured in an automatic device (KC 10; Amelung).

The thrombin clotting time (TT) is expressed as absolute values (seconds) as well as the ratio of TT without inhibitor ($TT_0$) to TT with inhibitor ($TT_i$). The latter ratios (range 1–0) are plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations are processed on a PC using the software program GraFit Version 3, setting equation equal to: Start at 0, define end=1 (Erithacus Software, Robin Leatherbarrow, Imperial College of Science, London, UK).

Test B

Determination of Thrombin Inhibition with a Chromogenic, Robotic Assay

The thrombin inhibitor potency is measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat No 3690). Stock solutions of test substance in DMSO (72 μL), 0.1–1 mmol/L, are diluted serially 1:3 (24+48 μL) with DMSO to obtain ten different concentrations, which are analysed as samples in the assay. 2 μL of test sample is diluted with 124 μL assay buffer, 12 μL of chromogenic substrate solution (S-2366, Chromogenix, Mölndal, Sweden) in assay buffer and finally 12 μL of α-thrombin solution (Human α-thrombin, Sigma Chemical Co. or Hematologic Technologies) in assay buffer, are added, and the samples mixed. The final assay concentrations are: test substance 0.00068–13.3 μmol/L, S-2366 0.30 mmol/L, α-thrombin 0.020 NIHU/mL. The linear absorbance increment during 40 minutes incubation at 37° C. is used for calculation of percentage inhibition for the test samples, as compared to blanks without inhibitor. The $IC_{50}$-robotic value, corresponding to the inhibitor concentration which causes 50% inhibition of the thrombin activity, is calculated from a log concentration vs. % inhibition curve.

Test C

Determination of the Inhibition Constant $K_i$ for Human Thrombin $K_i$-determinations are made using a chromogenic substrate method, performed at 37° C. on a Cobas Bio centrifugal analyser (Roche, Basel, Switzerland). Residual enzyme activity after incubation of human α-thrombin with various concentrations of test compound is determined at three different substrate concentrations, and is measured as the change in optical absorbance at 405 nm.

Test compound solutions (100 μL; normally in buffer or saline containing BSA 10 g/L) are mixed with 200 μL of human α-thrombin (Sigma Chemical Co) in assay buffer (0.05 mol/L Tris-HCl pH 7.4, ionic strength 0.15 adjusted with NaCl) containing BSA (10 g/L), and analysed as samples in the Cobas Bio. A 60 μL sample, together with 20 μL of water, is added to 320 μL of the substrate S-2238 (Chromogenix AB, Mölndal, Sweden) in assay buffer, and the absorbance change (ΔA/min) is monitored. The final concentrations of S-2238 are 16, 24 and 50 μmol/L and of thrombin 0.125 NIH U/mL.

The steady state reaction rate is used to construct Dixon plots, i.e. diagrams of inhibitor concentration vs. 1/(ΔA/min). For reversible, competitive inhibitors, the data points for the different substrate concentrations typically form straight lines which intercept at $x=-K_i$.

Test D
Determination of Activated Partial Thromboplastin Time (APTT)

APTT is determined in pooled normal human citrated plasma with the reagent PTT Automated 5 manufactured by Stago. The inhibitors are added to the plasma (10 μL inhibitor solution to 90 μL plasma) and incubated with the APTT reagent for 3 minutes followed by the addition of 100 μL of calcium chloride solution (0.025 M) and APTT is determined by use of the coagulation analyser KC10 (Amelung) according to the instructions of the reagent producer.

The clotting time is expressed as absolute values (seconds) as well as the ratio of APTT without inhibitor ($APTT_0$) to APTT with inhibitor ($APTT_i$). The latter ratios (range 1–0) are plotted against the concentration of inhibitor (log transformed) and fitted to sigmoidal dose-response curves according to the equation $$y=a/[1+(x/IC_{50})^S]$$

where: a=maximum range, i.e. 1; s=slope of the dose-response curve; and $IC_{50}$=the concentration of inhibitor that doubles the clotting time. The calculations are processed on a PC using the software program GraFit Version 3, setting equation equal to: Start at 0, define end=1 (Erithacus Software, Robin Leatherbarrow, Imperial College of Science, London, UK).

$IC_{50}$APTT is defined as the concentration of inhibitor in human plasma that doubled the Activated Partial Thromboplastin Time.

Test E
Determination of Thrombin Time ex vivo

The inhibition of thrombin after oral or parenteral administration of the compounds of the invention, dissolved in ethanol:Solutol™:water (5:5:90), is examined in conscious rats which, one or two days prior to the experiment, are equipped with a catheter for blood sampling from the carotid artery. On the experimental day blood samples are withdrawn at fixed times after the administration of the compound into plastic tubes containing 1 part sodium citrate solution (0.13 mol per L) and 9 parts of blood. The tubes are centrifuged to obtain platelet poor plasma.

50 μL of plasma samples are precipitated with 100 μL of cold acetonitrile. The samples are centrifuged for 10 minutes at 4000 rpm. 75 μL of the supernatant is diluted with 75 μL of 0.2% formic acid. 10 μL volumes of the resulting solutions are analysed by LC-MS/MS and the concentrations of thrombin inhibitor are determined using standard curves.

Test F
Determination of Plasma Clearance in Rat

Plasma clearance was estimated in male Sprague Dawley rats. The compound was dissolved in water and administered as a subcutaneous bolus injection at a dose of 4 μmol/kg. Blood samples were collected at frequent intervals up to 5 hours after drug administration. Blood samples were centrifuged and plasma was separated from the blood cells and transferred to vials containing citrate (10% final concentration). 50 μL of plasma samples are precipitated with 100 μL of cold acetonitrile. The samples are centrifuged for 10 minutes at 4000 rpm. 75 μL of the supernatant is diluted with 75 μL of 0.2% formic acid. 10 μL volumes of the resulting solutions are analysed by LC-MS/MS and the concentrations of thrombin inhibitor are determined using standard curves. The area under the plasma concentration-time profile was estimated using the log/linear trapezoidal rule and extrapolated to infinite time. Plasma clearance (CL) of the compound was then determined as $$CL=Dose/AUC$$

The values are reported in mL/min/kg.

Test G
Determination of in vitro Stability

Liver microsomes were prepared from Sprague-Dawley rats and human liver samples according to internal SOPs. The compounds were incubated at 37° C. at a total microsome protein concentration of 3 mg/mL in a 0.05 mol/L TRIS buffer at pH 7.4, in the presence of the cofactors NADH (2.5 mmol/L) and NADPH (0.8 mmol/L). The initial concentration of compound was 5 or 10 μmol/L. Samples were taken for analysis up to 60 minutes after the start of the incubation. The enzymatic activity in the collected sample was immediately stopped by adding 20% myristic acid at a volume corresponding to 3.3% of the total sample volume. The concentration of compound remaining (FINAL CONC) in the 60 min. sample was determined by means of LCMS using a sample collected at zero time as reference (START CONC). The % of degraded thrombin inhibitor was calculated as:

$$100\% \times \frac{[STARTCONC]-[FINALCONC]}{[STARTCONC]}$$

Test H
Arterial Thrombosis Model

Vessel damage was induced by applying ferric chloride ($FeCl_3$) topically to the carotid artery. Rats are anaesthetised with an intraperitoneal injection of sodium pentobarbital (80 mg/kg; Apoteksbolaget; Umeå, Sweden), followed by continuous infusion (12 mg/kg/h) throughout the experiment.

Rat body temperature was maintained at 38° C. throughout the experiment by external heating. The experiment started with a 5 minutes control period. Five minutes later, human $^{125}$I-fibrinogen (80 kBq; IM53; Amersham International, Buckinghamshire, UK) was given intravenously and was used as a marker for the subsequent incorporation of fibrin(ogen) into the thrombus. The proximal end of the carotid artery segment was placed in a plastic tube (6 mm; Silastic®; Dow Corning, Mich., USA) opened lengthways, containing $FeCl_3$-soaked (2 μL; 55% w/w; Merck, Darmstadt, Germany) filter paper (diameter 3 mm; IF; Munktell, Grycksbo, Sweden). The left carotid artery was exposed to $FeCl_3$ for 10 minutes and was then removed from the plastic tube and soaked in saline. Fifty minutes later, the carotid artery was removed and rinsed in saline. Reference blood samples were also taken for determination of blood $^{125}$I-activity, 10 minutes after the injection of $^{125}$I-fibrinogen, and at the end of the experiment. The $^{125}$I-activity in the reference blood samples and the vessel segment were measured in a gamma counter (1282 Compugamma; LKB Wallac Oy, Turku, Finland) on the same day as the experiment was performed. The thrombus size was determined as the amount of $^{125}$I-activity incorporated in the vessel segment in relation to the $^{125}$I-activity in the blood (cpm/mg).

The invention is illustrated by way of the following examples.

General Experimental Details

TLC was performed on silica gel.

Chiral HPLC analysis was performed using a 46 mm×250 mm Chiralcel OD column with a 5 cm guard column. The column temperature was maintained at 35° C. A flow rate of 1.0 mL/min was used. A Gilson 115 UV detector at 228 nm was used. The mobile phase consisted of hexanes, ethanol and trifluroacetic acid and the appropriate ratios are listed for each compound. Typically, the product was dissolved in a minimal amount of ethanol and this was diluted with the mobile phase.

LC-MS/MS was performed using a HP-1100 instrument equipped with a CTC-PAL injector and a 5 μm, 4×10 mm ThermoQuest, Hypersil BDS-C18 column. An API-3000 (Sciex) MS detector was used. The flow rate was 1.2 mL/min and the mobile phase (gradient) consisted of 10–90% acetonitrile with 90–10% of 4 mM aq. ammonium acetate, both containing 0.2% formic acid.

$^1$H NMR spectra were recorded using tetramethylsilane as the internal standard. $^{13}$C NMR spectra were recorded using the listed deuterated solvents as the internal standard.

Melting points are uncorrected.

EXAMPLE 1

Ph(3-Cl)(5-NHMe)-(R)CH(OH)C(O)-(S)Aze-Pab (i) Ph(3-Cl)(5-NHMe)-(R)CH(OH)C(O)OH

Method A:

A mixture of Ph(3-Cl)(5-NH$_2$)-(R)CH(OH)C(O)OH (3.5 g, 16.8 mmol; see international patent application WO 00/42059) and formaldehyde (1.8 mL of 37 wt % in H$_2$O, 23.9 mmol) in EtOH (400 mL) was stirred at 25° C. for 18 h. The solution was concentrated in vacuo to give a crushable foam that was combined with platinum(IV) oxide (0.35 g) in EtOH (400 mL) and stirred under a hydrogen atmosphere for 48 h. The mixture was filtered through a pad of Celite® and the filter cake washed with EtOH. The organics were concentrated in vacuo and flash chromatographed on silica gel eluting with CHCl$_3$:MeOH:concentrated NH$_4$OH (7:2.5:0.5) to afford 1.0 g (28%) of the ammonium salt of the sub-title compound as a crushable foam. The sub-title compound was obtained by flushing the corresponding ammonium salt through a pad of Amberlite® CG-50 with CH$_3$CN:MeOH (3:1).

Method B:

A mixture of Ph(3-Cl)(5-NH$_2$)-(R)CH(OH)C(O)OH (8.67 g, 43.0 mmol; see international patent application WO 00/42059) and methyl iodide (6.10 g, 43.0 mmol) in CH$_3$CN (500 mL) and MeOH (100 mL) was heated to 50° C. for 24 h. The solution was concentrated in vacuo and flash chromatographed on silica gel eluting with CHCl$_3$:MeOH:concentrated NH$_4$OH (7:2.5:0.5) to afford 2.9 g (31%) of the ammonium salt of the sub-title compound as a solid. The sub-title compound was obtained by flushing the corresponding ammonium salt through a pad of Amberlite® CG-50 with CH$_3$CN:MeOH (3:1).

Mp: 58–65° C.

$R_f$=0.25 (6:3:1 CHCl$_3$:MeOH:concentrated NH$_4$OH)

$^1$H NMR (300 MHz, CD$_3$OD) δ 6.68 (m, 1H), 6.61 (m, 1H), 6.50 (m, 1H), 4.98 (s, 1H), 2.75 (s, 3H).

$^{13}$C NMR (75 MHz, CD$_3$OD) δ 176.8, 153.4, 144.1, 136.7, 116.3, 113.2, 111.0, 74.7, 31.3

API-MS: (M+1)=216 m/z

HPLC Analysis: 97.2%, 97.9% ee, Chiralcel OD Column (90:10:0.5 Hex:EtOH:TFA mobile phase).

$[\alpha]_D^{25}$=−81.6° (c=1.0, MeOH)

(ii) Ph(3-Cl)(5-NHMe)-(R)CH(OH)C(O)-(S)Aze-Pab (Teoc)

To a mixture of Ph(3-Cl)(5-NHMe)-(R)CH(OH)C(O)OH (0.21 g, 0.97 mmol; see step (i) above) and H-(S)Aze-Pab (Teoc) (0.38 g, 1.02 mmol, see international patent application WO 00/42059) in DMF (10 mL) at 0° C. was added collidine (0.26 g, 2.13 mmol) and PyBOP (0.56 g, 1.07 mmol). The solution was stirred at 0° C. for 2 h, warmed to 25° C., stirred for 18 h and then concentrated in vacuo. Extensive flash chromatography (3×) on silica gel eluting first with CHCl$_3$:EtOH (9:1), then with CHCl$_3$:EtOH (95:5), and finally with EtOAc:EtOH (20:1) gave 0.31 g (61%) of the sub-title compound as a crushable foam.

Mp: 93–98° C.

$R_f$=0.40 (9:1 CHCl$_3$:EtOH)

$^1$H NMR (300 MHz, CD$_3$OD, mixture of rotamers) δ 7.82 (d, 2H, J=9 Hz), 7.42 (d, 2H, J=9 Hz), 6.66 (m, 1H), 6.48–6.59 (m, 2H), 5.13 and 4.78 (m, 1H), 5.02 (s, 1H) 3.96–4.58 (m, 6H), 2.76 (s, 3H), 2.05–2.75 (m, 2H), 1.05–1.13 (m, 2H), 0.07 (s, 9H)

API-MS: (M+1) 574 m/z (iii) Ph(3-Cl)(5-NHMe)-(R)CH(OH)C(O)-(S)Aze-Pab

To an ice-cold solution of Ph(3-Cl)(5-NHMe)-(R)CH(OH)C(O)-(S)Aze-Pab(Teoc) (71 mg, 0.12 mmol, from step (ii) above) in methylene chloride (10 mL) was added TFA (1 mL), and the mixture was stirred at 0° C. for 2 h and 1 h at rt, whereafter the resultant mixture was concentrated in vacuo. The remainder was dissolved in water and freeze-dried, yielding 79 mg (97%) of the title compound.

$^1$H NMR (500 MHz, CD$_3$OD): (complex due to diastereomers/rotamers) δ 7.74 (d, 2H), 7.52 (d, 2H); 7.03 (t, 0.25H, minor rotamer); 6.98 (t, 0.25H, minor rotamer); 6.96 (t, 0.75H, major rotamer); 6.93 (t, 0.25H, minor rotamer); 6.89 (t, 0.25H, major rotamer); 6.84 (t, 0.25H, major rotamer); 5.22 (dd, 0.25H, minor rotamer); 5.12 (s, 0.75H, major rotamer); 5.10 (s, 0.25H, minor rotamer); 4.80 (dd, 0.75H, major rotamer); 4.58–4.44 (several peaks, 2H); 4.34 (m, 0.75H, major rotamer); 4.12–3.95 (several peaks, 1.25H); 2.87 (s, 0.75H, minor rotamer); 2.83 (s, 2.25H, major rotamer); 2.70 (m, 0.25H, minor rotamer); 2.53 (s, 0.75H, major rotamer); 2.27 (m, 0.75H, major rotamer); 2.15 (s, 0.25H, minor rotamer).

$^{13}$C NMR (100 MHz, CDCl$_3$): (carbonyl and/or amidine carbons) δ 174.2; 173.6; 172.9; 168.1.

MS: (M+1) 430 m/z

EXAMPLE 2

Parallel synthesis of alkoxyamidines

This synthesis was performed in a 96-well Robbins block.

To a well containing an appropriate amount of O-substituted hydroxylamine (specified below) was added a solution of Ph(3-Cl)(5-NHMe)-(R)CH(OH)C(O)-(S)Aze-Pab(Teoc) (10 mg; 17 μmol; see Example 1(ii) above) in acetonitrile (1.0 mL). The block was sealed and the reaction mixture was rotated overnight in an oven at 60° C. After cooling and filtration, the solids were washed with acetonitrile (3×0.3 mL). The combined liquid fractions were concentrated in a vacuum centrifuge. The residue was partitioned between water (0.4 mL) and ethyl acetate (0.4 mL). Following liquid-liquid extraction everything was filtered through a column of Hydromatrix™. After washing three times with ethyl acetate, the combined filtrates were concentrated in a vacuum centrifuge. Deprotection was performed by addition of methylene chloride (0.1 mL) and trifluoroacetic acid (0.3 mL). After stirring at room temperature for 3 h the solvents were removed in vacuo. The residue was partitioned between sodium hydrogencarbonate (0.5 mL of a saturated aqueous solution) and ethyl acetate (0.5 mL). After extraction, filtration through Hydromatrix™ and concentration (vide infra), the residue was dissolved in isopropanol/water (7/3) (1 mL). About 2% of this solution was removed and diluted with isopropanol/water (7/3) (1 mL) for LC-MS analysis. After removal of the solvents in vacuo the solid residue was transferred to a 96-well plate using acetonitrile and ethyl acetate to dissolve the compound. The solvents were evaporated in a vacuum centrifuge to afford the following title compounds (all starting materials were commercially available):

2.1 Ph(3-Cl)(5-NHMe)-(R)CH(OH)C(O)-(S)Aze-Pab (OCH$_2$-3-isoxazole(5-Me))

Prepared using 3-[(aminooxy)methyl]-5-methylisoxazolexHCl (21 mg; 0.13 mmol). Yield: 4.66 mg (50%)

LC (254 mn) 100%

MS(m/z) 541 (M+1)$^+$ 2.2 Ph(3-Cl)(5-NHMe)-(R)CH(OH)C(O)-(S)Aze-Pab (OCH$_2$-3-pyridine)

Prepared using 3-[(aminooxy)methyl]pyridine×2 HCl (17 mg; 86 μmol).

Yield: 7.56 mg (81%).

LC: 100%

MS(m/z) 537 (M+1)$^+$ 2.3 Ph(3-Cl)(5-NHMe)-(R)CH(OH)C(O)-(S)Aze-Pab (OiBu)

Prepared using O-isobutylhydroxylaminexHCl (13 mg; 104 μmol). Yield: 4.9 mg (56%).

LC: 100%

MS(m/z) 502 (M+1)$^+$ 2.4 Ph(3-Cl)(-NHMe)-(R)CH(OH)C(O)-(S)Aze-Pab(OEt)

Prepared using O-ethylhydroxylaminexHCl (13 mg; 133 μmol). Yield: 7.13 mg (86%).

LC: 100%

MS(m/z) 474 (M+1)$^+$ 2.5 Ph(3-Cl)(5-NHMe)-(R)CH(OH)C(O)-(S)Aze-Pab(OBn)

Prepared using O-benzylhydroxylaminexHCl (18 mg; 113 μmol). Yield: 5.76 mg (62%).

LC: 100%

MS(m/z) 536 (M+1)$^+$ 2.6 Ph(3-Cl)(5-NHMe)-(R)CH(OH)C(O)-(S)Aze-Pab (OcHexyl)

Prepared using O-cyclohexylhydroxylaminexHCl (12 mg; 79 μmol).

Yield: 7.09 mg (77%).

LC: 100%

MS(m/z) 528 (M+1)$^+$ 2.7 Ph(3-Cl)(5-NHMe)-(R)CH(OH)C(O)-(S)Aze-Pab (OcButyl)

Prepared using O-cyclobutylhydroxylaminexHCl (16 mg; 130 μmol).

Yield: 6.24 mg (72%).

LC: 100%

MS(m/z) 500 (M+1)$^+$ 2.8 Ph(3-Cl)(5-NHMe)-(R)CH(OH)C(O)-(S)Aze-Pab (OCH$_2$-4-thiadiazole-(5-Cl))

Prepared using 4-(aminooxy)methyl-5-chloro-1,2,3-thiadiazolexHCl (16 mg; 79 μmol). Yield: 10.4 mg (100%).

LC: 100%

MS(m/z) 578 (M+1)$^+$ 2.9 Ph(3-Cl)(5-NHMe)-(R)CH(OH)C(O)-(S)Aze-Pab (OCH$_2$CH$_2$OPh(3-CF$_3$))

Prepared using O-[2-[3-(trifluoromethyl)phenoxy]ethyl] hydroxylaminexHCl (21 mg; 82 μmol). Yield: 7.44 mg (65%).

LC: 96%

MS(m/z) 634 (M+1)$^+$ 2.10 Ph(3-Cl)(5-NHMe)-(R)CH(OH)C(O)-(S)Aze-Pab (OBn(3-MeO))

Prepared using O-(3-methoxybenzyl)hydroxylaminex HCl (20 mg; 105 μmol). Yield: 5.07 mg (51%).

LC: 100%

MS(m/z) 566 (M+1)$^+$ 2.11 Ph(3-Cl)(5-NHMe)-(R)CH(OH)C(O)-(S)Aze-Pab (OBn(2-Br))

Prepared using O-(2-bromobenzyl)hydroxylaminexHCl (24 mg; 101 μmol). Yield: 5.01 mg (47%).

LC: 100%

MS(m/z) 616 (M+1)$^+$ 2.12 Ph(3-Cl)(5-NHMe)-(R)CH(OH)C(O)-(S)Aze-Pab (OBn(4-Me))

Prepared using O-(4-methylbenzyl)hydroxylaminexHCl (17 mg; 98 μmol).

Yield: 6.00 mg (63%).

LC: 100%

MS(m/z) 550 (M+1)$^+$ $^1$H NMR (400 MHz; CDCl$_3$): δ 7.99 (bt, 1H), 7.56 (d, 2H), 7.32 (d, 2H), 7.25 (d, 2H), 7.16 (d, 2H), 6.59 (t, 1H), 6.51 (t, 1H), 6.37 (t, 1H), 5.07 (s, 2H), 4.86 (bs, 1H), 4.84 (m, 2H), 4.76 (s, 1H), 4.44 (m, 2H), 4.03 (m, 1H), 3.70 (m, 1H), 2.75 (s, 3H), 2.60 (m, 1H), 2.35 (s, 3H), 2.34 (m, 1H).

$^3$C NMR (100 MHz; CDCl$_3$): (carbonyl and/or amidine carbons) δ 172.3, 171.1, 170.0, 151.8 or 150.9.

EXAMPLE 3

Ph(3-Cl)(5-NHMe)-(R)CH(OH)C(O)-(S)Aze-Pab(OMe)

(i) Ph(3-Cl)(5-NHMe)-(R)CH(OH)C(O)-(S)Aze-Pab(OMe, Teoc)

Ph(3-Cl)(5-NHMe)-(R)CH(OH)C(O)-(S)Aze-Pab(Teoc) (0.043 g; 0.075 mmol, see Example 1(ii) above) and O-methylhydroxylaminexHCl (0.045 g; 0.54 mmol) in THF (5 mL) were refluxed overnight. After concentration under reduced pressure, the residue was dissolved in ethyl acetate and washed with water and brine. Drying (Na$_2$SO$_4$) and removal of the solvent in vacuo afforded the sub-title compound as a colourless solid. Yield: 0.045 g (100%).

MS(m/z) 604 (M+1)$^+$, 602 (M-1)$^-$ (ii) Ph(3-Cl)(5-NHMe)-(R)CH(OH)C(O)-(S)Aze-Pab (OMe)

Trifluoroacetic acid (1.0 mL) was added to a stirred, ice/water-cooled solution of Ph(3-Cl)(5-NHMe)-(R)CH (OH)C(O)-(S)Aze-Pab(OMe, Teoc) (45 mg; 74 μmol; see step (i) above) in methylene chloride (10 mL). The cooling bath was removed after 1.5 h. After 1 h at rt, acetonitrile was added and the solvents were carefully removed under reduced pressure. The crude product was purified using reversed-phase HPLC (acetonitrile: 0.1 M aq. ammonium acetate) to afford, after freeze drying the appropriate fractions, the title compound as a colourless solid. Yield: 19 mg (56%).

MS(m/z) 460 (M+1)$^+$, 458 (M-1)$^-$ $^1$H NMR (300 MHz; CDCl$_3$): δ 8.02 (bt, 1H), 7.60 (d, 2H), 7.32 (d, 2H), 6.64 (s, 1H), 6.56 (s, 1H), 6.40 (s, 1H), 4.87 (m, 2H), 4.8 (s, 1H), 4.47 (m, 2H), 4.06 (m, 1H), 3.91 (s, 3H), 3.70 (m, 1H), 3.0 (bs, 1H), 2.80 (s, 3H), 2.65 (m, 1H), 2.40 (m, 1H).

$^{3}$C NMR (100 MHz; CD$_3$OD): (carbonyl and/or amidine carbons) δ 173.9, 172.7, 155.1.

EXAMPLE 4
Ph(3-Cl)(5-NHEt)-(R)CH(OH)C(O)-(S)Aze-Pab
(i) 3,5-Dinitrobenzylalcohol To a solution of 3,5-dinitrobenzoic acid (213.0 g, 1.00 mol) in anhydrous THF (1500 mL) at 0° C. was added borane-tetrahydrofuran complex (1.5 L of 1M in THF, 1.50 mol) over 1 h. The resulting heterogeneous mixture was stirred at 0° C. for 3 h and at 25° C. for 18 h. The resulting homogeneous solution was quenched with H$_2$O and concentrated in vacuo until solids were present. The solids were filtered, washed with H$_2$O and dissolved in EtOAc. The aqueous filtrate was extracted with EtOAc. The combined organics were washed with aqueous NaHCO$_3$ and brine, dried (Na$_2$SO$_4$), filtered and concentrated in vacuo to afford 176.0 g (89%) of the sub-title compound as a solid which was used without further purification.

$^1$H NMR (300 MHz, CD$_3$OD) δ 8.88 (m, 1H), 8.55–8.68 (m, 2H), 4.83 (s, 2H).

(ii) 3-Amino-5-nitrobenzyl alcohol

To a solution of 3,5-dinitrobenzyl alcohol (129.1 g, 0.65 mol; from step (i) above) in MeOH (1500 mL) at reflux was added ammonium sulfide (450 mL, 442.9 g of 20 wt % in H$_2$O, 1.30 mol) over 45 min. The resulting heterogeneous mixture was refluxed for 2 h and stirred at 25° C. for 18 h. The solution was filtered through a pad of Celite, the filtrate was acidified with 2N HCl and the MeOH distilled off in vacuo. The remaining acidic aqueous solution was washed with Et$_2$O (3×) and basified with 6N NaOH. The basic aqueous solution was extracted with Et$_2$O (4×). The organic extracts were dried (Na$_2$SO$_4$), filtered and concentrated in vacuo to afford 95.8 g (88%) of the sub-title compound as an orange solid which was used without further purification.

$^1$H NMR (300 MHz, CD$_3$OD) δ 7.46 (m, 1H), 7.38 (m, 1H), 6.98 (m, 1H), 4.57 (s, 2H).

(iii) 3-Chloro-5-nitrobenzyl alcohol

To a suspension of 3-amino-5-nitrobenzyl alcohol (103.8 g, 0.62 mol; from step (ii) above) in 1.0 L of 6N HCl at −5° C. was added sodium nitrite (47.1 g, 0.68 mol) in H$_2$O (400 mL) over 45 min. The resulting solution was stirred at −5° C. for 1 h prior to the addition of a mixture of copper(II) chloride (125.0 g, 0.93 mol) and copper(I)chloride (0.74 g, 0.007 mol) in 6N HCl (1.0 L) over 1 h while maintaining the temperature at less than 0° C. The resulting solution was warmed to 60–70° C. for 2.5 h then cooled to room temperature and extracted with Et$_2$O (6×). The organics were washed with brine (2×), dried (Na$_2$SO$_4$), filtered and concentrated in vacuo to give the crude product. Flash chromatography on silica gel eluting with Hex:EtOAc (4:1) gave 81.7 g (70%) of the sub-title compound as an off white solid. The sub-title compound could be further purified by crystallization from CH$_2$Cl$_2$.

Mp: 74–75° C.

$^1$H NMR (300 MHz, CDCl$_3$) δ 8.14 (s, 2H), 7.72 (s, 1H), 4.83 (d, 2H, J=7 Hz), 2.18 (t, 1H, J =7 Hz)

CI-MS: (M+1)=188 m/z (iv) 5-Amino-3-chlorobenzyl alcohol

Method A:

To a solution of 3-chloro-5-nitrobenzyl alcohol (31.0 g, 165 mmol; see step (iii) above) in EtOH (800 mL) was added platinum (IV) oxide (5 g). The suspension was stirred under one atmosphere of hydrogen for 24 h at room temperature. The reaction mixture was filtered through Celite® and the filter cake washed with EtOH. The filtrate was concentrated in vacuo to afford a brown oil which was flash chromatographed on silica gel eluting with Hex:EtOAc (1:1) to afford 12.1 g (46%) of the sub-title compound as an orange oil.

Method B:

To a solution of 3-chloro-5-nitrobenzyl alcohol (9.5 g, 50.6 mmol; see step (iii) above) in EtOAc (150 mL) was added 5% sulfided Pt/C (4.7 g). The suspension was stirred under one atmosphere of hydrogen for 5 h at room temperature. The reaction mixture was filtered through Celite® and the filter cake washed with EtOAc. The filtrate was concentrated in vacuo to afford 7.6 g (95%) of the sub-title compound as a solid, which was used without further purification.

$^1$H NMR (300 MHz, CD$_3$OD) δ 6.68 (s, 1H), 6.62 (m, 2H), 4.47 (s, 2H).

(v) 3-Chloro-5-(NHAc)benzyl acetate

To a solution of 5-amino-3-chlorobenzyl alcohol (14.1 g, 89.5 mmol; see step (iv) above) in pyridine (500 mL) at 0° C. was added dropwise acetic anhydride (36.5 g, 358 mmol). The mixture was warmed to room temperature and stirred for 5 h. The mixture was concentrated in vacuo and diluted with EtOAc (300 mL). The organics were successively washed with 2N HCl (3×300 mL), saturated NaHCO$_3$ (200 mL) and brine (200 mL) then dried (Na$_2$SO$_4$), filtered, and concentrated in vacuo to afford 20.5 g (95%) of the sub-title compound as a brown solid which was used without further purification.

$^1$H NMR (300 MHz, CDCl$_3$) δ 7.62 (bs, 1H), 7.52 (s, 1H), 7.34 (s, 1H), 7.02 (s, 1H), 5.02 (s, 2H), 2.17 (s, 3H), 2.10 (s, 3H)

(vi) 3-Chloro-5-(NHEt)benzyl alcohol

Lithium aluminum hydride (12.9 g, 339 mmol) was added in portions to a mechanically stirred solution of 3-chloro-5-(NHAc)benzyl acetate (20.5 g, 84.8 mmol; from step (v) above) in THF (600 mL) at 0° C. The suspension was refluxed for 3 h, cooled to 0° C., and successively quenched with H$_2$O (13 mL), 3N NaOH (13 mL) and H$_2$O (40 mL). The solids were removed by filtration over Celite® and washed with EtOAc (500 mL). The filtrate was concentrated in vacuo to give 15.7 g (100%) of the sub-title compound as an orange oil which was used without further purification.

$^1$H NMR (300 MHz, CDCl$_3$) δ 6.62 (s, 1H), 6.47 (s, 1H), 6.44 (s, 1H), 6.42 (s, 1H), 4.52 (s, 2H), 3.12 (q, J=7.5 Hz, 2H), 1.25 (t, J=7.5 Hz, 3H)

(vii) 3-Chloro-5-(NHEt)benzaldehyde

Oxalyl chloride (12.0 g, 94.8 mmol) was added dropwise to a solution of dimethyl sulfoxide (14.8 g, 190 mmol) in CH$_2$Cl$_2$ (400 mL) at −78° C. After 30 min at −78° C., a solution of 3-chloro-5-(NHEt)benzyl alcohol (15.7 g, 86.2 mmol; from step (vi) above) in CH$_2$Cl$_2$ (250 mL) was added dropwise over 30 min. After 30 min at −78° C., diisopropylethylamine (55.7 g, 431 mmol) was added dropwise, and the mixture was warmed to room temperature overnight. The mixture was successively washed with 1N HCl (1.0 L), H$_2$O (500 mL) and brine (2×500 mL), dried (Na$_2$SO$_4$), and concentrated in vacuo to give a brown oil. Flash chromatography on silica gel eluting with Hex:EtOAc (7:1) afforded 6.40 g (40%) of the sub-title compound as a yellow solid.

$^1$H NMR (300 MHz, CDCl$_3$) δ 9.87 (s, 1H), 7.10 (s, 1H), 6.90 (s, 1H), 6.77 (s, 1H), 3.90 (bs, 1H), 3.20 (m, 2H), 1.25 (t, J=7.5 Hz, 3H)

(viii) 3-Chloro-5-(NEt)-5-(N-trifluoroacetyl)benzaldehyde

Trifluoroacetic anhydride (9.26 g, 44.1 mmol) was added dropwise to a solution of 3-chloro-5-(NHEt)benzaldehyde (5.40 g, 29.4 mmol; from step (vii) above) and pyridine (3.49 g, 44.1 mmol) in $CH_2Cl_2$ (150 mL) at 0° C. The mixture was warmed to room temperature and stirred overnight. The mixture was successively washed with saturated $Na_2CO_3$ (150 mL) and 1N HCl (150 mL), dried ($Na_2SO_4$), filtered, and concentrated in vacuo to give 7.46 g (91%) of the sub-title compound as a yellow solid which was used without further purification.

$^1$H NMR (300 MHz, $CDCl_3$) δ 10.0 (s, 1H), 7.91 (s, 1H), 7.62 (s, 1H), 7.50 (s, 1H),3.80 (m, 2H), 2H), 1.20 (t, J=7.5 Hz, 3H)

(ix) Ph(3-Cl)(5-NEt)(5-N-trifluoroacetyl)-CH(OTMS)CN

To a solution of 3-chloro-5-(NEt)-5-(N-trifluoroacetyl) benzaldehyde (7.46 g, 26.7 mmol; from step (viii) above) in $CH_2Cl_2$ (150 mL) at 0° C. was added $ZnI_2$ (425 mg, 1.34 mmol) and trimethylsilyl cyanide (2.90 g, 29.3 mmol). The solution was stirred overnight at room temperature. The mixture was washed with $H_2O$ (100 mL), dried ($Na_2SO_4$), filtered, and concentrated in vacuo to afford 9.30 g (92%) of the sub-title compound as an orange oil which was used without further purification.

$^1$H NMR (300 MHz, $CDCl_3$) δ 7.58 (s, 1H), 7.29 (s, 1H), 7.24 (s, 1H), 5.52 (s, 1H), 3.80 (q, J=7.5 Hz, 2H), 1.20 (t, J=7.5 Hz, 3H), 0.30 (s, 9H)

(x) Ph(3-Cl)(5-NHEt)-(R,S)CH(OH)C(O)OH

Ph(3-Cl)(5-NEt)(5-N-trifluoroacetyl)CH(OTMS)CN (1.40 g, 3.69 mmol; from step (ix) above) was refluxed in concentrated HCl (10 mL) for 6 h at which time, the mixture was concentrated in vacuo to give a brown solid. Flash chromatography on silica gel eluting with $CHCl_3$:MeOH:concentrated $NH_4OH$ (6:3:1) afforded the ammonium salt of the sub-title compound which was dissolved in $H_2O$, acidified (pH~5) with 1M HCl and extracted with EtOAc (3×15 mL). The combined organics were dried ($Na_2SO_4$), filtered, and concentrated in vacuo to afford 540 mg (64%) of the sub-title compound as a brown solid.

$^1$H NMR (300 MHz, $CD_3OD$) δ 6.69 (s, 1H), 6.64 (s, 1H), 6.54 (s, 1H), 5.03 (s, 1H), 3.10 (q, J=7.1 Hz, 2H), 1.21 (t, J=7.2 Hz, 3H)

(xi) Ph(3-Cl)(5-NHEt)-(R)CH(OH)C(O)OH (a) and Ph(3-Cl)(5-NHEt)-(S)CH(OAc)C(O)OH (b)

A mixture of Ph(3-Cl)(5-NHEt)-(R,S)CH(OH)C(O)OH (540 mg, 2.36 mmol; from step (x) above) and Lipase PS "Amano" (280 mg) in vinyl acetate (15 mL) and MTBE (15 mL) was heated at reflux for 22 h. The reaction mixture was filtered through Celite® and the filter cake washed with EtOAc (100 mL). The filtrate was concentrated in vacuo and subjected to flash chromatography on silica gel eluting with $CHCl_3$:MeOH:concentrated $NH_4OH$ (6:3:1) yielding the ammonium salts of the sub-title compounds (a) and (b). The ammonium salt of the sub-title compound (a) was taken up in EtOAc (10 mL) and neutralized with 2M HCl in $Et_2O$ (0.65 mL). Water (10 mL) was added, and the layers were separated. The aqueous layer was extracted with EtOAc (2×20 mL), and the combined organic extracts were dried ($Na_2SO_4$), filtered, and concentrated in vacuo to afford 260 mg (48%) of the sub-title compound (a) as a white solid. The ammonium salt of the sub-title compound (b) (260 mg, 46%) was used without further manipulation or characterization.

For sub-title compound (a):
$^1$H NMR (300 MHz, $CD_3OD$) δ 6.69 (s, 1H), 6.64 (s, 1H), 6.54 (s, 1H), 5.03 (s, 1H), 3.10 (q, J=7.1 Hz, 2H), 1.21 (t, J=7.2 Hz, 3H)

For sub-title compound (b):
$^1$H NMR (300 MHz, $CD_3OD$) δ 6.69 (s, 1H), 6.65 (s, 1H), 6.56 (s, 1H), 5.70 (s, 1H), 3.08 (q, J=7.1 Hz, 2H), 2.14 (s, 3H), 1.20 (t, J=7.2 Hz, 3H)

(xii) Ph(3-Cl)(5-NEt)-(R)CH(OH)C(O)-(S)Aze-Pab(Teoc)

To a solution of Ph(3-Cl)(5-NHEt)-(R)CH(OH)C(O)OH (260 mg, 1.22 mmol; sub-title compound (a) from step (xi) above) and H-(S)Aze-Pab(Teoc) (602 mg, 1.34 mmol) in DMF (10 mL) at 0° C. was added PyBOP (698 mg, 1.34 mmol) and collidine (517 mg, 4.27 mmol). The solution was stirred at 0° C. for 2 h and then warmed to room temperature and stirred overnight. The mixture was partitioned with EtOAc (3×50 mL) and $H_2O$ (50 mL). The combined organics were dried ($Na_2SO_4$), filtered, and concentrated in vacuo. Flash chromatography on silica gel eluting with $CHCl_3$:MeOH (20:1) followed by rechromatography (2×) eluting with EtOAc:EtOH (20:1) afforded 157 mg (22%) of the sub-title compound as a white solid.

Mp: 95–100° C.

$R_f$=0.40 (15:1 $CHCl_3$:MeOH)

$^1$H NMR (300 MHz, $CD_3OD$, mixture of rotamers) δ 7.80 (d, J=8.2 Hz, 2H), 7.41 (d, J=8.2 Hz, 2H), 6.63 (s, 1H), 6.57 (s, 1H), 6.53 (s, 1H), 5.10–5.15 (m, 1H), 5.00 (s, 1H), 4.74–4.81 (m, 1H), 4.20–4.52 (m, 5H), 3.90–4.10 (m, 2H), 3.07 (q, J=7.2 Hz, 2H), 2.44–2.68 (m, 1H), 2.14–2.33 (m, 1H), 1.21 (t, J=7.1 Hz, 3H), 1.08 (t, J=8.6 Hz, 2H), 0.08 (s, 9H)

API-MS (M+1)=588 m/z (xiii) Ph(3-Cl) (5-NHEt)-(R)CH(OH)C(O)-(S)Aze-Pab

TFA (4.0 mL) was added to a solution of Ph(3-Cl)(5-NHEt)-(R)CH(OH)C(O)-(S)Aze-Pab(Teoc) (0.090 g, 0.15 mmol; from step (xii) above) in DCM (2 mL) at rt. The reaction mixture was stirred for 15 minutes. The solvent was evaporated without heating. The product was dissolved in acteonitrile and water (1:5) and freeze-dried to yield 70 mg (68%) of the title compound.

$^1$H NMR (500 MHz; $D_2O$): δ 7.70–7.12 (m, 7H), 5.23–4.72 (m, 2H), 4.40–3.92 (m, 5H), 3.24 (m, 2H), 2.55 (m, 1H), 2.10 (m, 1H), 1.14 (m, 3H)

LC-MS (m/z) 444 (M+1)$^+$

EXAMPLE 5

Ph(3-Cl)(5-NHAc)-(R)CH(OH)C(O)-(S)Aze-Pab (i) Ph(3-Cl)(5-NHAc)-(R)CH(OH)C(O)OH

A solution of Ph(3-Cl)(5-$NH_2$)-(R)CH(OH)C(O)OH (1.5 g, 7.44 mmol; see international patent application WO 00/42059) in pyridine (100 mL) at 0° C. was treated with acetic anhydride (0.77 mL, 0.84 g, 8.18 mmol). After 30 min, additional acetic anhydride (0.35 mL) was added and the reaction was warmed to 25° C. After 1 h, a third aliquot of acetic anhydride (0.17 mL) was added and the reaction was stirred at 25° C. for 18 h. The solution was concentrated in vacuo, the residue dried, dissolved in MeOH, made basic with 2 N NaOH and stirred for 3 h. The solution was neutralized with excess Amberlite CG-50 and filtered through a pad of Celite. The organics were concentrated in vacuo and flash chromatographed on silica gel eluting with $CHCl_3$:MeOH:concentrated $NH_4OH$ (7:2.5:0.5) to afford 1.5 g (83%) of the ammonium salt of the sub-title compound as a solid with a chiral purity of 89% ee by chiral HPLC analysis.

Due to the low chiral purity of the sub-title compound, the corresponding salt was neutralized with Amberlite CG-50 and subjected to enzymatic resolution (0.3 g Lipase PS Amano; 20 mL MTBE; 20 mL vinyl acetate; 55° C.; 18 h). Filtration through Celite followed by concentration and flash chromatography on silica gel eluting with $CHCl_3$:MeOH:concentrated $NH_4OH$ (6:3:1) afforded 1.0 g of the ammonium salt of the sub-title compound as a crushable foam. The sub-title compound was obtained as a solid by partitioning the corresponding ammonium salt between 1 M HCl and EtOAc and concentrating the organics in vacuo.

Mp: 155–157° C.

$R_f$=0.25 (6:3:1 CHCl$_3$:MeOH:concentrated NH$_4$OH)

$^1$H NMR (300 MHz, CD$_3$OD) δ 7.76 (m, 1H), 7.49 (m, 1H), 7.22 (s, 1H), 5.12 (s, 1H), 2.13 (s, 3H).

$^{13}$C NMR (75 MHz, CD$_3$OD) δ 175.5, 172.0, 143.6, 141.4, 135.5, 123.2, 120.5, 117.6, 73.5, 24.0.

API-MS: (M+1)=244 m/z

HPLC Analysis: 96.3%, 95.7% ee, Chiralcel OD Column (92:8:0.5 Hex:EtOH:TFA mobile phase).

$[\alpha]_D^{25}$=−99.4° (c=1.0, MeOH)

(ii) Ph(3-Cl)(5-NHAc)-(R)CH(OH)C(O)-(S)Aze-Pab(Teoc)

To a mixture of Ph(3-Cl)(5-NHAc)-(R)CH(OH)C(O)OH (0.25 g, 1.01 mmol; see step (i) above) and H-(S)Aze-Pab (Teoc) (0.40 g, 1.06 mmol, see international patent application WO 00/42059) in DMF (15 mL) at 0° C. was added collidine (0.27 g, 2.22 mmol) and PyBOP (0.58 g, 1.11 mmol). The solution was stirred at 0° C. for 2 h, warmed to 25° C. and stirred for 18 h then concentrated in vacuo. The residue was dissolved in EtOAc and washed with H$_2$O and brine. The organics were dried (Na$_2$SO$_4$), filtered and concentrated in vacuo. Extensive flash chromatography (3×) on silica gel eluting first with CHCl$_3$:EtOH (95:5) then second with CH$_2$Cl$_2$:MeOH:concentrated NH$_4$OH (94:5:1) and last with CH$_2$Cl$_2$:MeOH:concentrated NH$_4$OH (88.5:10:1.5) gave 0.40 g (66%) of the sub-title compound as a crushable foam.

Mp: 65–72° C.

$R_f$=0.45 (9:1 CH$_2$Cl$_2$:MeOH)

$^1$H NMR (300 MHz, CD$_3$OD, mixture of rotamers) δ 7.79 (d, 2H, J=9 Hz), 7.68 (m, 1H), 7.35–7.53 (m, 3H), 7.18 and 7.15 (m, 1H), 5.18 and 4.79 (m, 1H), 5.14 and 5.09 (s, 1H), 3.93–4.55 (m, 6H), 2.05–2.78 (m, 2H), 2.12 (s, 3H), 1.03–1.13 (m, 2H), 0.08 (s, 9H).

API-MS: (M+1)=602 m/z (iii) Ph(3-Cl)(5-NHAc)-(R)CH(OH)C(O)-(S)Aze-Pab

To a solution of Ph(3-Cl)(5-NHAc)-(R)CH(OH)C(O)-(S)Aze-Pab(Teoc) (0.11 g, 0.18 mmol; see step (ii) above) in 2 mL of CH$_2$Cl$_2$ was added 2 mL of TFA. The mixture was allowed to react for 4 h and subsequently evaporated. The crude product was purified using PHPLC (C8 column, 50×250 mm, gradient: 0 to 50% CH$_3$CN, 60 mL/min). After evaporation the residue was freeze dried from water-acetic acid. Yield: 95 mg of the title compound as an acetate salt (99%).

$^1$H NMR (500 MHz, D$_2$O, mixture of rotamers): δ 7.66 (m, 2H), 7.50 (m, 1H minor rotamer), 7.45–7.35 (m, 3H), 7.22 (m, 1H), 7.07 (m, 1H minor rotamer), 5.25 (m, 1H rotamer), 5.15–5.10 (m, 2H rotamer) 4.84 (m, 1H rotamer), 4.55–4.45 (m, 2H rotamer), 4.41 (m, 1H rotamer), 4.28 (d, 1H rotamer), 4.18–3.95 (m, 2H rotamer), 2.78 (m, 1H rotamer), 2.58 (m, 1H rotamer), 2.35–2.16 (m, 1H), 2.13 (s, 3H rotamer), 2.11 (s, 3H rotamer), 1.92 (s, 3H).

$^{13}$C NMR (125 MHz, D$_2$O): δ 173.9, 173.1, 173.0, 172.80, 172.76, 172.6, 166.6, 166.5.

MS: (M+1) 458 m/z

EXAMPLE 6

Ph(3-Cl)(5-NHAc)-(R)CH(OH)C(O)-(S)Aze-Pab(OiPr)

A mixture of Ph(3-Cl)(5-NHAc)-(R)CH(OH)C(O)-(S)Aze-Pab(Teoc) (60 mg, 0.10 mmol; see Example 5(ii) above) and H$_2$NOiPr×HCl (70 mg, 0.63 mmol) in THF (5 mL) was heated to 60° C. overnight. The solvent was evaporated and the crude was partitioned between water and EtOAc. The water phase was extracted with EtOAc and the organic layers were dried (Na$_2$SO$_4$) and concentrated to give 65 mg (100%) of the title compound. The crude material was dissolved in DCM (2 mL) at rt, TFA (2.0 mL) was added and the reaction mixture was stirred for 1 hour. The solvent was evaporated without heating and the crude was partitioned between water and EtOAc. The water phase was extracted with EtOAc and the organic phase was dried (Na$_2$SO$_4$) and concentrated. The crude was subjected to flash chromatography using DCM:MeOH (95:5) as eluent. The product was further purified with preparative RPLC (CH$_3$CN:0.1M NH$_4$OAc-buffered, 0–50%), the fractions of interest were concentrated and the product was freeze-dried to yield 50 mg (94%) of the title compound.

$^1$H NMR (400 MHz; CD3OD): δ 7.70–7.12 (m, 7H), 5.20–4.72 (m, 2H), 4.48–3.92 (m, 5H), 2.73–2.11 (m, 2H), 2.10 (s, 3H), 1.26 (s, 3H), 1.24 (s, 3H).

$^{13}$C NMR (100 MHz, CD3OD): (carbonyl and/or amidine carbons) δ 172.3; 171.5; 170.6

LC-MS (m/z) 517 (M+1)$^+$

EXAMPLE 7

The title compounds of Examples 1, 4 and 5 were tested in Test A above and were found to exhibit an IC$_{50}$TT value of less than 0.02 μM.

EXAMPLE 8

The title compounds of Examples 1, 4 and 5 were tested in Test D above and were found to exhibit an IC$_{50}$APTT value of less than 1 μM.

EXAMPLE 9

Title compounds of Examples 2 and 3 were tested in Test G above and were found to be converted to the corresponding active inhibitor (free amidine) in liver microsomes from humans and rats.

EXAMPLE 10

The title compounds of Examples 3 and 6 were tested in Test E above and were found to exhibit oral and/or parenteral bioavailability in the rat as the corresponding active inhibitor (free amidine).

| Abbreviations | | |
|---|---|---|
| Ac | = | acetyl |
| AcOH | = | acetic acid |
| API | = | atmospheric pressure ionisation (in relation to MS) |
| AUC | = | area under the curve |
| Aze | = | azetidine-2-carboxylate |
| AzeOH | = | azetidine-2-carboxylic acid |
| BSA | = | bovine serum albumin |
| Bn | = | benzyl |
| Bu | = | butyl |
| Bzl | = | benzyl |
| CI | = | chemical ionisation (in relation to MS) |
| d | = | day(s) |
| DCC | = | dicyclohexyl carbodiimide |
| DCM | = | dichloromethane |
| DIPEA | = | diisopropylethylamine |
| DMAP | = | 4-(N,N-dimethyl amino) pyridine |
| DMF | = | dimethylformamide |
| DMSO | = | dimethylsulfoxide |
| EDC | = | 1-(3-dimethylaminopropyl)-3-ethylcarbodiimide hydrochloride |
| Et | = | ethyl |
| Et$_2$O | = | diethyl ether |
| ether | = | diethyl ether |
| EtOAc | = | ethyl acetate |
| EtOH | = | ethanol |

Abbreviations

| | | |
|---|---|---|
| h | = | hour(s) |
| HATU | = | O-(azabenzotriazol-1-yl)-N,N,N',N'-tetramethyluronium hexafluorophosphate |
| HBTU | = | [N,N,N',N'-tetramethyl-O-(benzotriazol-l-yl)uronium hexafluorophosphate] |
| HCl | = | hydrochloric acid |
| HCl(g) | = | hydrogen chloride gas |
| Hex | = | hexanes |
| HOAc | = | acetic acid |
| HPLC | = | high performance liquid chromatography |
| LC | = | liquid chromatography |
| Me | = | methyl |
| MeOH | = | methanol |
| Mp | = | melting point |
| MS | = | mass spectroscopy |
| MTBE | = | methyl tert-butyl ether |
| NADH | = | nicotinamide adenine dinucleotide, reduced form |
| NADPH | = | nicotinamide adenine dinucleotide phosphate, reduced form |
| NIH | = | National Institute of Health (US) |
| NIHU | = | National Institute of Health units |
| Pab | = | para-amidinobenzylamino |
| H-Pab | = | para-amidinobenzylamine |
| Ph | = | phenyl |
| PHPLC | = | preparative high performance liquid chromatography |
| Pr | = | propyl |
| PyBOP | = | (benzotriazol-1-yloxy)tripyrrolidinophosphonium hexafluorophosphate |
| QF | = | tetrabutylammonium fluoride |
| RPLC | = | reverse phase high performance liquid chromatography |
| rt | = | room temperature |
| SOPs | = | standard operating procedures |
| TBTU | = | [N,N,N',N'-tetramethyl-O-(benzotriazol-1-yl)uronium tetrafluoroborate] |
| TEA | = | triethylamine |
| Teoc | = | 2-(trimethylsilyl)ethoxycarbonyl |
| TFA | = | trifluoroacetic acid |
| THF | = | tetrahydrofuran |
| THP | = | tetrahydropyranyl |
| TLC | = | thin layer chromatography |
| TMSCN | = | trimethylsilyl cyanide |
| Z | = | benzyloxycarbonyl |

Prefixes n, s, i and t have their usual meanings: normal, secondary, iso and tertiary. The prefix c means cyclo.

What is claimed is:

1. A compound of formula I,

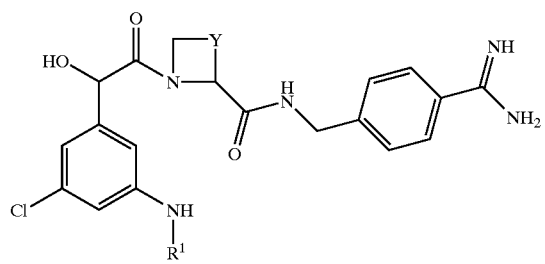

wherein

R$^1$ represents C(O)CH$_3$ or C$_{1-3}$ alkyl; and

Y represents —CH$_2$— or —(CH$_2$)$_2$, or a pharmaceutically-acceptable salt or prodrug thereof.

2. A compound as claimed in claim 1, wherein Y represents —CH$_2$—.

3. A compound as claimed in claim 1, wherein R$^1$ represents C(O)CH$_3$, methyl or ethyl.

4. A compound as claimed in claim 1 which is Ph(3-Cl)(5-NHMe)—CH(OH)C(O)-Aze-Pab or a pharmaceutically-acceptable salt or prodrug thereof.

5. A compound as claimed in claim 1 which is Ph(3-Cl)(5-NHAc)-CH(OH)C(O)-Aze-Pab or a pharmaceutically-acceptable salt or prodrug thereof.

6. A pharmaceutically acceptable salt of a compound of formula I as defined in claim 1, which salt compound is a compound of formula Ia,

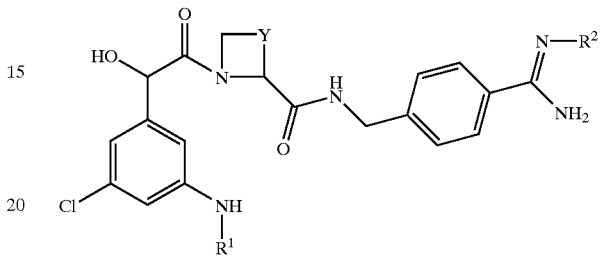

wherein R$^2$ represents OR$^3$ or C(O)OR$^4$;

R$^3$ represents H, C$_{1-10}$ alkyl, C$_{1-3}$ alkylaryl or C$_{1-3}$ alkyloxyaryl (the alkyl parts of which latter two groups are optionally interrupted by one or more oxygen atoms, and the aryl parts of which latter two groups are unsubstituted or substituted by one or more substituents selected from halo, phenyl, methyl or methoxy, which latter three groups are also unsubstituted or substituted by one or more halo substituents);

R$^4$ represents C$_{1-10}$ alkyl (which latter group is optionally interrupted by one or more oxygen atoms), or C$_{1-3}$ alkylaryl or C$_{1-3}$ alkyloxyaryl (the alkyl parts of which latter two groups are optionally interrupted by one or more oxygen atoms, and the aryl parts of which latter two groups are unsubstituted or substituted by one or more substituents selected from halo, phenyl, methyl or methoxy, which latter three groups are also unsubstituted or substituted by one or more halo substituents); and R$^1$ and Y are as defined in claim 1, or a pharmaceutically-acceptable salt thereof.

7. A compound as claimed in claim 6, wherein R$^2$ represents OR$^3$.

8. A compound as claimed in claim 7, wherein R$^3$ represents: H; unsubstituted, linear, branched or cyclic C$_{1-8}$ alkyl; C$_{1-3}$ alkyloxyphenyl, the phenyl group of which is unsubstituted or substituted by one or more substituents as defined above; or C$_{1-2}$ alkylaryl, wherein the aryl group is phenyl, pyridinyl, isoxazolyl or thiadiazolyl, which latter four groups are unsubstituted or substituted by one or more substituents as defined above.

9. A compound as claimed in claim 8, wherein R$^3$ represents: linear C$_{1-6}$ alkyl, or cyclic C$_{3-6}$ alkyl; or methylaryl, wherein the aryl group is phenyl or isoxazolyl, which latter two groups are unsubstituted or substituted in the aryl part by one substituent selected from methoxy, methyl and bromo.

10. A compound as claimed in claim 9, wherein R$^3$ represents methyl, ethyl, i-propyl, cyclohexyl, 4-methylbenzyl, 3-methoxybenzyl, 2-bromobenzyl or 5-methyl-3-isoxazolyl.

11. A compound as claimed in claim 1, wherein the

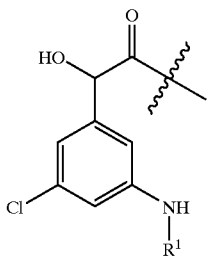

moiety is in the R-configuration.

12. A compound as claimed in claim 1, wherein the

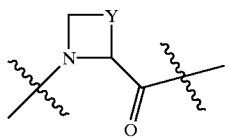

moiety is in the S-configuration.

13. A compound as claimed in claim 1 which is Ph(3-Cl)(5-NHMe)-(R)CH(OH)C(O)-(S)Aze-Pab or a pharmaceutically acceptable salt or prodrug thereof.

14. A compound as claimed in claim 1 which is Ph(3-Cl)(5-NHAc)-(R)CH(OH)C(O)-(S)Aze-Pab or a pharmaceutically acceptable salt or prodrug thereof.

15. A pharmaceutical formulation including a compound as defined in claim 1, or a pharmaceutically acceptable salt or prodrug thereof, in admixture with a pharmaceutically acceptable adjuvant, diluent or carrier.

16. A method of treatment of a condition where inhibition of thrombin is required which method comprises administration of a therapeutically effective amount of a compound as defined in claim 1, or a pharmaceutically acceptable salt thereof, to a person suffering from, or susceptible to, such a condition.

17. A method of treatment of a condition where anticoagulant therapy is indicated which method comprises administration of a therapeutically effective amount of a compound as defined in claim 1, or a pharmaceutically acceptable salt thereof, to a person suffering from, or susceptible to, such a condition.

18. A method as claimed in claim 16, wherein the condition is thrombosis.

19. A method as claimed in claim 16, wherein the condition is hypercoagulability in blood and/or tissues.

20. A process for the preparation of a compound of formula I, as defined in claim 1 which comprises:
(i) reacting of a compound of formula II

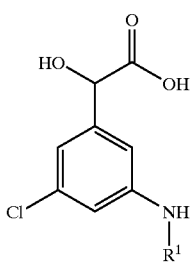

wherein $R^1$ is as defined in claim 1, with a compound of formula III,

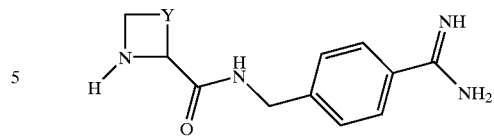

wherein Y is as defined in claim 1;
(ii) reacting of a compound of formula IV,

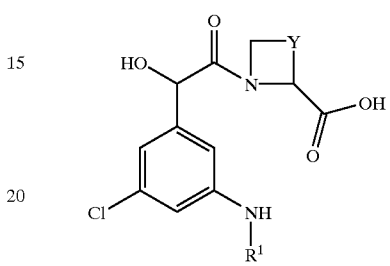

wherein $R^1$ and Y are as defined in claim 1, with para-amidinobenzylamine; or (iii) deprotection of a protected derivative of a compound as defined in claim 1.

21. A compound of formula II as defined in claim 20 or a protected derivative thereof.

22. A compound as claimed in claim 21 which is Ph(3-Cl)(5-NHMe)-CH(OH)C(O)OH or a protected derivative thereof, or Ph(3-Cl)(5-NHAc)-CH(OH)C(O)OH or a protected derivative thereof.

23. A compound of formula IV, as defined in claim 20, or a protected derivative thereof.

24. A compound as claimed in claim 23 which is Ph(3-Cl)(5-NHMe)-CH(OH)C(O)-Aze-OH or a protected derivative thereof, or Ph(3-Cl)(5-NHMe)—CH(OH)C(O)-Aze-OH or a protected derivative thereof.

25. A process for the preparation of a compound of formula Ia as defined in claim 6, which comprises:
(a) reacting of a compound of formula II as defined in claim 20 with a compound of formula XII,

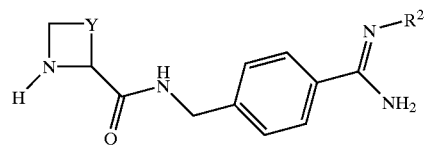

wherein Y is as defined in claim 1 and $R^2$ is as defined in claim 6;

(b) reacting of a compound of formula IV, as defined in claim 20, with a compound of formula XIII,

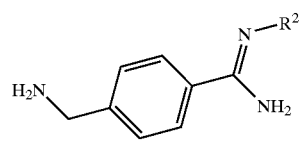

wherein $R^2$ is as defined in claim 6;

(c) for compounds of formula Ia in which $R^2$ represents OH, reaction of a corresponding compound of formula XIV,

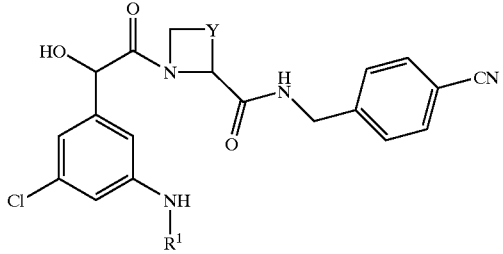

XIV wherein $R^1$ and Y are as defined in claim 1, with hydroxylamine;

(d) for compounds of formula Ia in which $R^2$ represents $OR^3$, reaction of a compound of formula XV,

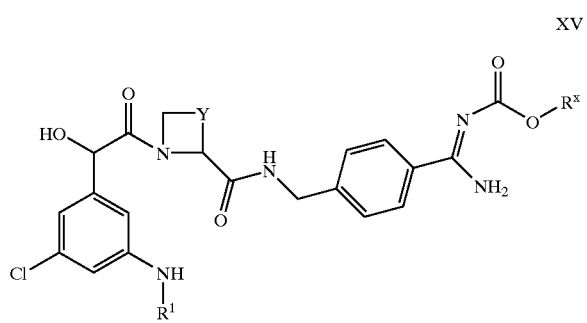

XV wherein $R^x$ represents $—CH_2CH_2—Si(CH_3)_3$ or benzyl, and $R^1$ and Y are as defined in claim 1, or a tautomer thereof, with a compound of formula XVI, $$R^3ONH_2 \qquad \text{XVI}$$

wherein $R^3$ is as defined in claim 6, or an acid addition salt thereof, followed by removal of the $—C(O)OR^x$ group;

(e) for compounds of formula Ia in which $R^2$ represents $COOR^4$, reaction of a corresponding compound of formula I, as defined in claim 1, with a compound of formula XVII, $$L^1COOR^4 \qquad \text{XVII}$$

wherein $L^1$ represents a leaving group, and $R^4$ is as defined in claim 6; or (f) for compounds of formula Ia in which $R^2$ represents $OCH_3$ or $OCH_2CH_3$, reaction of a corresponding compound of formula Ia in which $R^2$ represents OH with dimethylsulfate or diethylsulfate, respectively.

26. A compound of formula XIV, as defined in claim 25, or a protected derivative thereof.

27. A compound of formula XV, as defined in claim 25, or a protected derivative thereof.

28. A compound as claimed in claim 27 which is Ph(3-Cl)(5-NHMe)-CH(OH)C(O)-Aze-Pab(Teoc) or a protected derivative thereof, or Ph(3-Cl)(5-NHMe)—CH(OH)C(O)-Aze-Pab(Teoc) or a protected derivative thereof.

* * * * *